(12) United States Patent
Ranade et al.

(10) Patent No.: US 9,920,000 B2
(45) Date of Patent: Mar. 20, 2018

(54) SYNTHESIS OF METHYL CARBAMATE AND DIMETHYL CARBONATE (DMC) IN PRESENCE OF STRIPPING WITH INERT GAS OR SUPERHEATED VAPOURS AND A REACTOR FOR THE SAME

(71) Applicant: COUNCIL OF SCIENTIFIC & INDUSTRIAL RESEARCH, New Delhi (IN)

(72) Inventors: Vivek Vinayak Ranade, Pune (IN); Ashutosh Anant Kelkar, Pune (IN); Vilas Hari Rane, Pune (IN); Anil Kisan Kinage, Pune (IN); Savita Kiran Shingote, Pune (IN); Lalita Sanjib Roy, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 124 days.

(21) Appl. No.: 14/441,753

(22) PCT Filed: Nov. 11, 2013

(86) PCT No.: PCT/IB2013/002498
§ 371 (c)(1),
(2) Date: May 8, 2015

(87) PCT Pub. No.: WO2014/072803
PCT Pub. Date: May 14, 2014

(65) Prior Publication Data
US 2015/0315134 A1    Nov. 5, 2015

(30) Foreign Application Priority Data

Nov. 9, 2012   (IN) .......................... 3490/DEL/2012

(51) Int. Cl.
| | | |
|---|---|---|
| *C07C 269/00* | (2006.01) | |
| *B01J 8/02* | (2006.01) | |
| *B01J 19/00* | (2006.01) | |
| *B01J 8/20* | (2006.01) | |
| *C07C 68/06* | (2006.01) | |
| *B01J 19/24* | (2006.01) | |
| *C07C 68/00* | (2006.01) | |
| *B01J 8/18* | (2006.01) | |

(52) U.S. Cl.
CPC ........... *C07C 269/00* (2013.01); *B01J 8/0207* (2013.01); *B01J 8/1818* (2013.01); *B01J 8/1827* (2013.01); *B01J 8/1836* (2013.01); *B01J 8/20* (2013.01); *B01J 19/0013* (2013.01); *B01J 19/24* (2013.01); *C07C 68/00* (2013.01); *C07C 68/06* (2013.01); *B01J 2208/00123* (2013.01); *B01J 2219/00006* (2013.01); *B01J 2219/182* (2013.01); *Y02P 20/582* (2015.11)

(58) Field of Classification Search
None
See application file for complete search history.

(56) References Cited

U.S. PATENT DOCUMENTS

| | | |
|---|---|---|
| 4,436,668 A | 3/1984 | Harder et al. |
| 6,392,078 B1 | 5/2002 | Ryu et al. |
| 2002/0082439 A1 | 6/2002 | Ryu et al. |
| 2008/0221367 A1 | 9/2008 | Hollander et al. |
| 2012/0130111 A1 | 5/2012 | Koh et al. |

FOREIGN PATENT DOCUMENTS

| | | |
|---|---|---|
| WO | 02096851 A1 | 12/2002 |
| WO | 2006024655 A1 | 3/2006 |
| WO | 2011013880 A2 | 2/2011 |

OTHER PUBLICATIONS

International Search Report dated Mar. 17, 2014 (PCT/IB2013/002498); ISA/EP.

*Primary Examiner* — Alicia L Otton
*Assistant Examiner* — Po-Chih Chen
(74) *Attorney, Agent, or Firm* — Banner & Witcoff, Ltd.

(57) ABSTRACT

The invention relates to synthesis of methyl carbamate (MC) and dimethyl carabonate (DMC) in presence of stripping inert gas or superheated methanol vapors using packed column reactor and bubble column reactor.

11 Claims, 5 Drawing Sheets

SYNTHESIS OF METHYL CARBAMATE AND DIMETHYL CARBONATE (DMC) IN PRESENCE OF STRIPPING WITH INERT GAS OR SUPERHEATED VAPOURS AND A REACTOR FOR THE SAME

CROSS-REFERENCE TO RELATED APPLICATIONS

This application is a U.S. National Phase filing of International Application No. PCT/IB2013/002498, filed Nov. 11, 2013, designating the United States of America, and claiming priority to Indian Patent Application No. 3490/DEL/2012, filed Nov. 9, 2012, and this application claims priority to and the benefit of the above-identified applications.

The following specification particularly describes the invention and the manner in which it is to be performed:

FIELD OF THE INVENTION

The invention relates to synthesis of dimethyl carbonate (DMC) employing homogeneous or heterogeneous catalyst in the presence of stripping inert gas or superheated vapors using packed bed reactor or bubble column reactor. More particularly, present invention relates to synthesis of methyl carbamate (MC) in the presence of stripping inert gas or superheated vapors using packed bed reactor or bubble column reactor.

BACKGROUND AND PRIOR ART OF THE INVENTION

Dimethyl carbonate (DMC) is an important intermediate and is widely used in industry. Owing to its low toxicity, dimethyl carbonate is considered a "green" chemical product with bright development prospects. DMC is a versatile chemical and has been used mainly as a methylating and methoxy carbonylating agent as a safe substitute for dimethyl sulphate, phosgene or methyl halide, which are toxic or corrosive. It can also be used as a solvent to replace halogenated solvents. DMC has a high octane number and could be a good additive for gasoline in the future and could lead to increase in demand of DMC. This increasing focus on the use of DMC is mainly due to the bio-degradability, with a low bioaccumulation as well as its low toxicity.

Presently, DMC is produced mainly from methanol and phosgene in concentrated NaOH solution. Because of the use of phosgene for its production, DMC has been limited in industrial use. DMC also can be produced by non-phosgene route which includes oxidative carbonylation of methanol in liquid phase, which is put on stream in the EniChem Ravenna factory using CuCl catalyst. The major drawbacks of this process are low production rate; high cost of separation of products and reactants, high recycle requirements and the need for corrosion resistant reactor and process lines. Another non-phosgene process is the synthesis of DMC by transesterification of cyclic carbonate with methanol developed by Asahi Kasei Chemical, Japan. The main disadvantages of the route are: the slow reaction rate of epoxides with $CO_2$ and requirement of high pressures, and the exchange reaction of the cyclic carbonate with methanol are limited by equilibrium.

The economy of the process is affected due to the use of epoxide which is expensive and formation of ethylene glycol as a by-product in stoichiometric quantity.

$CO_2$ as a readily available, inexpensive and environmentally acceptable material has been widely investigated as raw material for DMC synthesis. But still the progress made so far is not satisfactory due to the difficulty of activation of $CO_2$, and thermodynamic limitations.

Synthesis of DMC by the reaction of urea and methanol is an attractive alternative route. This will be a GREEN Process, being based on cheap and renewable raw materials. The reaction scheme is presented below:

Scheme 1

Urea → Methyl carbamate (1)

Methyl carbamate → Dimethyl carbonate (2)

Methyl carbamate + Dimethyl carbonate → Methyl-N-methyl carbamate (3)

Dimethyl carbonate → Dimethyl ether (4)

There are several patents as well as publications in recent times on the synthesis of DMC from methanol and urea as enumerated below:

U.S. Pat. No. 4,436,668 relates to preparation of carbonates of formula I, by reacting a carbamic acid ester of the formula II;

with an alcohol of the formula $R^1$—OH (wherein $R^1$ and $R^2$ have the meanings as described in said patent), in presence of stripping gas and in presence or absence of a catalyst. The final product is removed from the mixture by fractional distillation. This patent does not talk about mode of operation for the reactor used (batch or continuous) and also range of carbonates covered is higher. For higher dialkyl carbonates products are nonvolatile and only ammonia is removed during inert gas stripping. The details regarding stripping of product carbonates along with ammonia are not elaborated in the patent. Thus it is not clear how the stripping is carried out. This is crucial, since product dialkyl carbonates are also not stable under reaction conditions and can undergo decarboxylation reaction.

An article titled "High-Yield Synthesis of Dimethyl Carbonate from Urea and Methanol Using a Catalytic Distillation Process" by Mouhua Wang, Hui Wang et. al. in Ind. Eng. Chem. Res. 2007, 46, 2683-2687 relates to catalytic distillation technique for DMC synthesis which minimizes other side reactions. The article further discloses DMC yield of 60-70% by catalytic distillation reactor over a Zn-based catalyst. In this method DMC formed as a product is removed from the reaction as it is formed and the distillation condenser has a reflux ratio adjusted. Because of this product DMC is removed from the reaction mixture and part of the DMC product along with solvent methanol is returned back to the reactor. DMC returning to the reaction mixture can further react to form MMC as by-product or decompose to form DME, thus reducing overall yield of the DMC.

An article titled "Synthesis of dimethyl carbonate from urea and methanol using polyphosphoric acid as catalyst" by Jianjun Sun et. al in Journal of molecular catalysis A. chemical 239 (2005) 82-86 disclose synthesis of DMC from urea and methanol in a batch operation. Polyphosphoric acid (PPA) is used as catalyst and absorbent for ammonia produced during the reaction. Drawback of this approach is that the phosphoric acid reacts with ammonia formed and is consumed during the reaction.

It is obvious that for any reversible reaction, removal of at least one of the products from the reacting medium will drive the reaction in a forward direction. However, most of the prior art emphasizes on stripping ammonia from reactant mass and not on removal of DMC from the reactant mass. The inert gases used in the prior art include $N_2$, $CO_2$, Argon, He, ethane, methane and propane. However, none of the prior art disclose stripping with superheated vapors which have several advantages over previously disclosed stripping agents.

In some existing prior arts that disclose use of catalytic distillation, stripping may occur within the portion of catalytic distillation column. In these cases reflux ratio is fixed and this can lead to part of DMC product returning back to the reactor. DMC is known to decompose in the presence of catalysts and this can lead to loss in the yield of DMC. However, this stripping is with saturated methanol and in counter-current fashion which happens in any distillation column with stripping section. Further, there is no prior disclosure on any other form of stripping.

The inventors of the instant invention observed that through efficient removal of by-product, ammonia is necessary to shift the equilibrium in forward direction, simultaneous effective removal of DMC can reduce decomposition of DMC thereby enhancing the yield and selectivity. But prior arts do not provide effective means to perform the same. To overcome this gap in the art, the inventors have realized the removal of DMC by using packed bed reactor and sectionalized bubble column reactor.

Further, while packed bed reactor and bubble column reactors are known in the art, it is however, desired to provide a bubble column reactor with improved configuration that can allow significantly better stripping than that of packed column (counter-current stripping) or stirred reactors or vertical bubble column reactors. It is further desirable to provide horizontal sectionalized bubble column reactor with one or many sections configured to allow stripping of both ammonia and DMC simultaneously, which is not known in the art.

OBJECTS OF INVENTION

Main object of the present invention is to provide an efficient process for synthesis of methyl carbamate (MC) and dimethyl carbonate (DMC) using packed bed reactor or bubble column reactor.

Another object of the present invention is to provide an improved process by removing ammonia and DMC by stripping using inert gas and superheated vapors.

BRIEF DESCRIPTION OF THE FIGURES

FIG. 1 represents MC and/or DMC reactor with inert gas stripping [100]. A simple reactor is shown in FIG. 1 with the facility of inert gas stripping. The pressure inside is controlled by the back pressure regulator [109]. Reactants enter the reactor through feed inlet [104]. Inert gases or superheated vapors are fed through the single or multiple inlets [103] where the feed pressure is maintained by the pressure regulator. There is arrangement to properly distribute gases or superheated vapors [102] into the liquid pool formed above. Vapor outlet stream is then passed through the condenser [110] to separate the non-condesables from condensables.

FIG. 2 represents Horizontal, sectionalized bubble column reactor [200]. The schematic of the Sectionalized horizontal bubble column reactor is shown in FIG. 2. This reactor may have one or several compartments [201] through which the feed passes in succession. Reactant mixture is fed through the feed inlet [204] which can either be the fresh feed or the recycled unreacted reactants and stripping gas or vapor through gas inlet [203]. The pressure inside reactor is maintained by the back pressure regulator [209]. Stripping gas is appropriately distributed by the gas distribution arrangement [203] into the liquid pool formed above. Suitable heat transfer device is provided to maintain the reactor temperature within a stipulated range. There is arrangement for the liquid phase outlet [206], however, this may or may not be used. Vapor product [207] is drawn and sent to condenser [210] to separate condensables and non-condensables.

FIG. 4 depicts Packed-bed reactor set-up. Here Urea/Methyl carbamate solution in methanol is brought into contact with properly distributed stripping gas (Superheated methanol vapors in this case) in counter current mode in a Packed bed reactor. The condenser condenses the vapours and the pressure inside is maintained with the help of a back pressure regulator giving out non-condensables. Bottom product cooler cools the liquid product out of the bottom portion of the reactor so that they can be stored and analyzed.

6 depicts the Bubble column reactor set-up in actual with single section. Here the Urea/Methyl carbamate solution is fed from the top of the reactor. The feed pipe is immersed directly into the liquid pool inside and properly distributed stripping gas is introduced through the bottom of the reactor. Vapor product is drawn from the reactor and passed through the condenser. The condensable products are collected in the vapor product collector and non-condensables are vented to the scrubbing system through back pressure regulator which maintains stipulated pressure inside the reactor.

SUMMARY OF THE INVENTION

Accordingly, present invention provides a process for synthesis of methyl carbamate and dimethyl carbonate (DMC) in reactor comprising:
   a. feeding liquid reactant feed comprising of urea and methanol or methyl carbamate and methanol into a reactor vessel [201] containing expanded slurry bed of solid catalyst particles suspended in a suspension liquid or in a packed bed of solid catalyst and allowing to react;
   b. passing the inert gas or superheated methanol vapours into said reactor vessel [201] through inlet valve [203] by regulating the pressure to ensure positive flow of the inert gas and stripping ammonia and DMC formed during the reaction through the outlet port [207];
   c. passing the product gases collected from the outlet port [207] through condenser [209] and gas-liquid separator [210];
   d. removing liquid phase products from the reactor [200] through liquid outlet post [206];
   e. optionally, recycling methanol or gaseous product into the reactor vessel for further reaction through inlet port [204].

In an embodiment of the present invention, homogeneous catalyst is used the catalyst will be soluble in the reaction mixture.

In another embodiment of the present invention, reactor used is selected from packed bed reactors and bubble column reactors having counter-current and cross-current stripping preferably horizontal bubble column AND horizontal sectionalized bubble column reactors [200].

In yet another embodiment of the present invention, optionally the reaction is carried out in presence of catalyst selected from the group consisting of hydrotalcite and hydrotalcite like compounds, double metal cyanides, cenosphere or ionic liquids.

In yet another embodiment of the present invention, the process step (a) is carried out in a reactor comprising feeding liquid reactant feed comprising of urea and methanol or methyl carbamate and methanol into a reactor vessel [201] containing an expanded slurry bed of solid catalyst particles suspended in a suspension liquid or in a packed bed of solid catalyst and allowing to react or in a packed bed of solid catalyst and allowing to react.

In yet another embodiment of the present invention, the concentration of catalyst particles present in the slurry bed is in the range of 0.01 to 10 weight percentage. In yet another embodiment of the present invention, the inert gas is selected from air, $CO_2$, He, Ar, N2 and such like.

In yet another embodiment of the present invention, velocity of inert gas or superheated methanol vapors used for stripping ammonia and DMC is in the range of $1 \times 10^{-4}$ to 0.1 m/s.

In yet another embodiment of the present invention, pressure in step (b) is regulated by maintaining a constant pressure difference between constant pressure regulator fitted to an inlet valve and back pressure regulator fitted to an outlet valve to ensure positive flow of inert gas.

In yet another embodiment of the present invention, the temperature of the reactor is maintained at a temperature in the range of 130-210° C.

In yet another embodiment of the present invention, the process is batch or continuous.

In yet another embodiment of the present invention, the ratio of recycle gas stream/liquid reactant feed is in the range of 0.5 to 15.

In yet another embodiment, present invention provides a horizontal sectionalized bubble column reactor [200] for synthesis of methyl carbamate and dimethyl carbonate (DMC) comprising:
   a. reactor with single or multiple compartments [201] to receive liquid reactant feed comprising of urea and methanol or methyl carbamate and methanol through the inlet ports [204] for the reaction to occur;
   b. Gas distributor chamber [202] located within the cylindrical bubble column reactor [200] comprising a plate intersecting the cylinder with or without an angle to the axis of the cylinder [200];
   c. Single or multiple inlet ports [203] fitted to the Gas distributor chamber [202] for distributing gas;
   d. Single or multiple inlet ports [203] fitted with constant pressure regulator, single or multiple gas/vapor outlet ports [207] fitted with back pressure regulator [209] for gaseous phase, wherein, the pressure difference of 10 psi is maintained to ensure positive flow of inert gas into the reactor [201];
   e. Single or multiple liquid outlet ports [206] with in-line filter [206a] fitted to reactor [200] for liquid phase withdrawal;
   f. Heat transfer device [208] fitted to the reactor [200] for maintaining temperature of the reaction;
   g. Condenser and gas-liquid separator [210] fitted to the outlet ports [207] wherein the product in vapor form is condensed and separated from the liquid components;
   h. Outlet for condensate [211] and Outlet for non-condensate [212] connected to gas-liquid separator [210].

In yet another embodiment of the present invention, the reactor [201] optionally comprises an expanded slurry bed of solid catalyst particles suspended in a suspension liquid or in a packed bed of solid catalyst.

In yet another embodiment, present invention provides horizontal sectionalized bubble column reactor comprising a recycling inlet for recycling methanol or gaseous product into the reactor vessel for further reaction through inlet port [204].

DETAILED DESCRIPTION OF INVENTION

Present invention provides a process for synthesis of methyl carbamate and dimethyl carbonate from methanol and urea in a horizontal sectionalized bubble column reactor with one or many sections, that enables cross flow stripping, thus significantly increasing process efficiency by not only stripping ammonia and/or DMC from the reaction mixture but also significantly reducing decomposition of DMC to DME and formation of MMC by stripping DMC.

The synthesis of methyl carbamate (MC) can be carried out using methanol and urea in the presence or absence of catalyst and the synthesis of dimethyl carbonate (DMC) can be carried out using methanol and urea or methyl carbamate in presence of catalyst selected from hydrotalcite, double metal cyanide, cenosphere or ionic liquids. The catalyst can be homogeneous (soluble in the reaction mixture) or heterogeneous (insoluble in the reaction mixture) in the form of a slurry in the reaction mixture.

For the first step (Conversion of urea to MC) catalyst is not used and only stripping by inert gas or superheated methanol is sufficient to get MC with very high conversion and selectivity.

The reactants are in liquid state, products are obtained in vaporized phase and the catalyst if used is in solid state. Catalyst can be in liquid state if homogeneous catalyst is used The conversion of urea to methyl carbamate (MC) and MC to DMC steps can be performed in a single vessel comprising different sections in the instant horizontal bubble column reactor.

Accordingly, present invention provides an efficient process for synthesis of methyl carbamate and dimethyl carbonate (DMC) in a horizontal sectionalized bubble column reactor and the said process comprising the steps of:

a. feeding liquid reactant feed comprising of urea and methanol or methyl carbamate and methanol into a reactor vessel [200] containing expanded slurry bed of solid catalyst particles suspended in a suspension liquid or in a packed bed of solid catalyst and allowed to react; If the catalyst is homogeneous then it will be in a dissolved state in the bubble column;

b. passing the inert gas or superheated vapours into said reactor vessel through inlet valve [203] by regulating the pressure to ensure positive flow of the inert gas or superheated vapours and stripping methanol, DMC and ammonia formed during the reaction through the outlet port [207], c. pressurizing the reactor [200] with the inert gas and closing the inert valve;

d. heating the vessel and opening the inlet valve [204] after attaining desired temperature and further heating;

e. collecting methanol, DMC and ammonia dissolved in methanol in a reservoir after passing through cooled condenser connected to Back Pressure Regulator outlet (vapor phase outlet);

f. optionally recycling methanol or gaseous product into the reactor vessel for further reaction through inlet port [204];

g. cooling the reactor to room temperature after completion of reaction, collecting the reaction mixture in the vapor phase from the outlet ports [206];

h. condensing in a condenser and gas liquid separator [210]; and subjecting for further analysis.

The reaction step (b) may be carried out in presence of a homogeneous or heterogeneous catalyst. If heterogeneous catalyst is used the reactor vessel contain an expanded slurry bed of solid catalyst particles suspended in a suspension liquid or in a packed bed of solid catalyst on which reactant feed is allowed to react. If homogeneous catalyst is used, the bubble column reactor will comprise of gas-liquid dispersion and the packed column reactor will comprise inert packings.

The present invention provides horizontal sectionalized bubble column reactor [200] for synthesis of methyl carbamate and dimethyl carbonate (DMC) comprising;

a. reactor with single or multiple compartments [201] to receive liquid reactant feed comprising of urea and methanol or methyl carbamate and methanol through the inlet ports [204] for the reaction to occur;

b. Gas distributor chamber [202] within the cylindrical bubble column reactor comprising a plate intersecting the cylinder with or without an angle to the axis of the cylinder;

c. Single or multiple inlet ports [203] fitted to the Gas distributor chamber for distributing gas;

d. Single or multiple inlet ports [204] fitted with constant pressure regulator, single or multiple outlet ports [207] fitted with back pressure regulator [209] for gaseous phase, wherein, the pressure difference of 10 psi is maintained to ensure positive flow of inert gas into the reactor [201];

e. Single or multiple outlet ports [206] with in-line filter [206a] fitted to reactor [201] for liquid phase;

f. Heat transfer device [208] fitted to the reactor [201] for maintaining temperature of the reaction;

g. Condenser and gas-liquid separator [210] fitted to the outlet ports [206] wherein the product in vapor form is condensed and separated from the liquid components;

h. Outlet for condensate [211] and Outlet for non-condensate [212]

The present invention provides MC and DMC reactor with inert gas stripping [100] comprising;

1. gas-liquid-solid reactor [101] [gas in the form of bubbles, solids could either in suspended particles or packed bed];
2. Gas distributor [102] [pipe type, sieve plate, bubble cap, any other type];
3. Single or multiple inlet ports [103] for gas phase;
4. Single or multiple inlet ports [104] for liquid phase;
5. Single or multiple measurement and/or control ports [105];
6. Single or multiple outlet ports [106] for liquid phase;
7. Single or multiple outlet ports [107] for gas phase;
8. Heat transfer device [108];
9. Back pressure regulator [109];
10. Condenser and gas-liquid separator [110]:
11. Outlet for condensate [111];
12. Outlet for non-condensate [112].

The present invention relates to process for synthesis of methyl carbamate (MC) and dimethyl carbonate (DMC) using methanol and urea or methyl carbamate and methanol in presence of inert gas or superheated vapors as stripping agent. The process is realized in a horizontal sectionalized bubble column reactor with one or many sections. The horizontal sectionalized bubble column reactor used in the instant invention allows cross flow stripping, where the inert gas or the stripper flows horizontally at right angles, or cross flow, to the liquid. Cross flow stripping has an advantage over conventional counter current stripping. In a typical stripping operation, the mass transfer coefficient is insensitive to the velocity of the gas stream. Moreover, the advantages of cross flow stripping are low pressure drop in the column and greater vapor flow rates without flooding enabling the reaction to proceed in forward direction thereby enhancing the selectivity and yield.

The cross flow stripping tower is a geometry that increases the cross section of gas flow while making minimal disturbances to the liquid flow, allowing high gas-liquid ratios without flooding. Although, cross flow towers offers a number of advantages over counter current towers, their use has been hampered due to lack of adequate design procedures.

The present invention offers sectionalized horizontal bubble column reactor with improved configurations that offers unprecedented flexibility and versatility to carry out effectively synthesis of methyl carbamate and dimethyl carbonate. This reactor has distinct advantage over conventional mass transfer equipment that we have cross flow type phase contacting. The distinction can be made on the basis of mass transfer characteristics and its role in pushing the reaction forward increasing conversion and maintaining reasonable selectivity. We can use higher stripping gas flow rates which is not possible in conventional column due operational restrictions such as high pressure drop and flooding.

The overall process performance can be enhanced by appropriate selection of inert gas, method of sparging, flow rate of inert gas, method of collecting and separating the sparged gas.

The overall process performance can be enhanced by sparging vapours of superheated methanol, method of sparging, flow rate of methanol vapours.

The inert gas which is sparged into the reactor vessel is selected from air, $CO_2$, He, Ar, $N_2$ and such like.

The reaction may be carried out in absence or presence of the catalyst. When a catalyst is used it may be selected from catalyst selected from hydrotalcite, double metal cyanide, cenospheres or ionic liquid.

Figure 1:
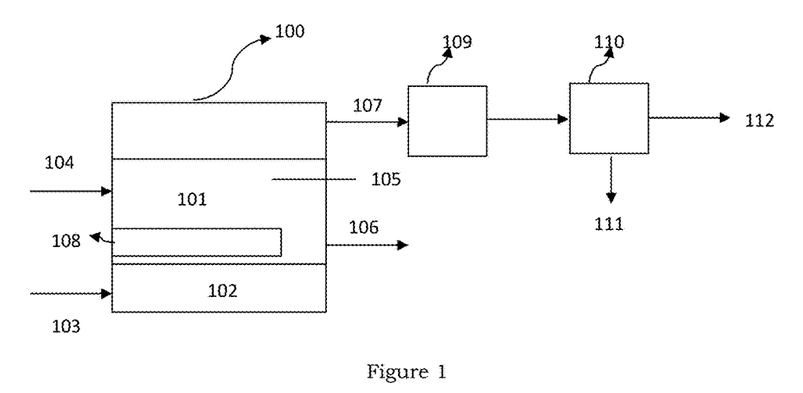
Figure 2:
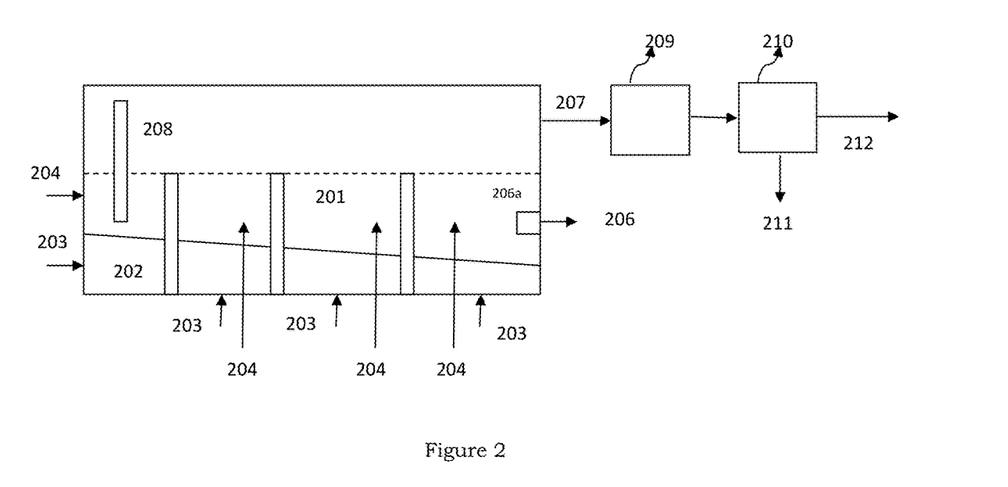

The horizontal sectionalized bubble column reactor used for the synthesis of methyl carbamate (MC) and dimethyl carbonate (DMC) is now detailed herein below with reference to FIGS. 1 and 2 provided therein.

The MC and/or DMC reactor [100] with inert gas stripping in a horizontal bubble column reactor [200] comprises single or multiple compartments [201]. The reactor is fed with liquid feed reactants and is fitted with single or multiple inlet ports [204] for passing liquid reactant feed, a heat transfer device [208] which helps in maintaining the heat of the reaction and single or multiple outlet ports [206] for liquid phase with in-line filter [206a]. This would be required to withdraw liquid from the reactor and filter would be useful to keep heterogeneous catalyst inside reactor should we use that type of catalyst.

The gas distributor [202] in the form of pipes, sieve plates, bubble cap or any such type is realized within the cylindrical bubble column reactor by using a plate intersecting the cylinder with or without an angle to the axis of the cylinder; wherein the angle and the distributor characteristics within each compartment is tailored to realize desired distribution of gas within different compartments. The gas distributor chamber [202] has single or multiple inlet ports for passing gas into the distributor chamber. The distributor chamber is fitted to the reactor with single or multiple compartments [201] through inlet pipes [204] fitted with constant pressure regulator.

The reactor is fixed with single or multiple outlet ports [207], for gaseous components, which is attached to back pressure regulator [209]. A condenser and gas liquid separator [210] is attached to the reactor with an outlet [211] and an outlet [212] for non-condensate.

The reactor contains expanded slurry bed of solid catalyst particles suspended in a suspension liquid or in a packed bed of solid catalyst (not shown in the fig) when a catalyst is used. When homogeneous catalyst is used catalyst will be soluble in the reaction medium.

In the process, the liquid reactant feed comprising of urea and methanol or methyl carbamate and methanol are charged into the reactor [201] through single or multiple inlet ports [204]. Inert gas or superheated methanol vapours as a stripping agent contained in the gas distributor [202] is fed into the reactor through gas inlet valve [203] which is fitted with constant pressure regulator. On initiation of the reaction, ammonia and methanol formed during the reaction are stripped out through the outlet valve [207] which is fitted with back pressure regulator [209].

The pressure difference of 10 psi is maintained between constant pressure regulator and back pressure regulator to ensure positive flow of stripping gas or superheated methanol vapours. The reactor [201] is further pressurized with stripping gas at requisite pressure during which the inlet valve [203] is closed while keeping the outlet valve open [207]. The contents are heated under very slow stirring condition. On attaining the temperature, the inlet valve [203] is opened and the reaction is continued for 1-3 hours. Methanol along with ammonia and DMC formed as product are expelled due to positive pressure of stripping gas are collected in a trap (cooled with ice and salt mixture) connected to Back Pressure Regulator outlet (vapor outlet). After completion of reaction, the reactor [201] is cooled to room temperature. The reaction mixture obtained in the gaseous state is collected in the condenser and separated in gas liquid separator [210] and further analyzed separately by HPLC and Gas Chromatography for urea, MC and DMC analysis respectively.

In the process, optionally the methanol or methyl carbamate formed initially is recycled into the reactor vessel for further reaction.

The inert gas or superheated methanol vapours are passed into the reactor [201] at a velocity ranging from $1.2 \times 10^{-4}$ m/s to 0.017 m/s for 60 to 180 minutes.

The pressure at the constant pressure regulator and at back pressure regulator may be varied according to the nature of the gas used, the liquid reactants and the catalyst used, however, the pressure difference of 10 psi is maintained between constant pressure regulator and back pressure regulator to ensure positive flow of stripping gas. The temperature of the reactor is operated at a temperature in the range of 130-190° C.

The reactor [201] has an internal diameters ranging from 25 mm to 800 mm and the slurry bed/solution pool has an expanded height ranging from 12 mm to 400 mm. and diameter in the range of 25 to 75 mm. The concentration of catalyst present in the slurry bed or in the homogeneous phase (for soluble catalysts) is in the range of 0.04 to 0.12 mol/lit.

The synthesis of present invention may be carried out continuously or batchwise.

The ratio of recycle gas stream/liquid reactant feed is in the range of 0.5 to 15.

The reactor vessel [202] is provided with a heat transfer device [208] that maintains the desired temperature of the reaction.

In an optional embodiment, the reaction may be carried out in presence of a catalyst. When a catalyst is used in the process, the reactor comprises of expanded slurry bed of solid catalyst particles suspended in a suspension liquid or in a packed bed of solid catalyst on which the reaction between urea and methanol or methyl carbamate and methanol is effected. When homogeneous catalyst is used the catalyst will be soluble in the reaction mixture.

The synthesis of methyl carbamate or dimethyl carbonate from urea and methanol may be operated with the overall conversion rate of urea in the range of 96-98%.

The synthesis reaction may be operated at a selectivity towards methyl carbamate (MC) in the range of 85-99% and of DMC at a selectivity in the range of 35 to 75%.

In an embodiment, conversion of urea to MC and MC to DMC can be combined in a single vessel comprising different sections by varying pressure and temperature conditions accordingly in different sections to minimize utility consumption while improving the selectivity.

Figure 3:
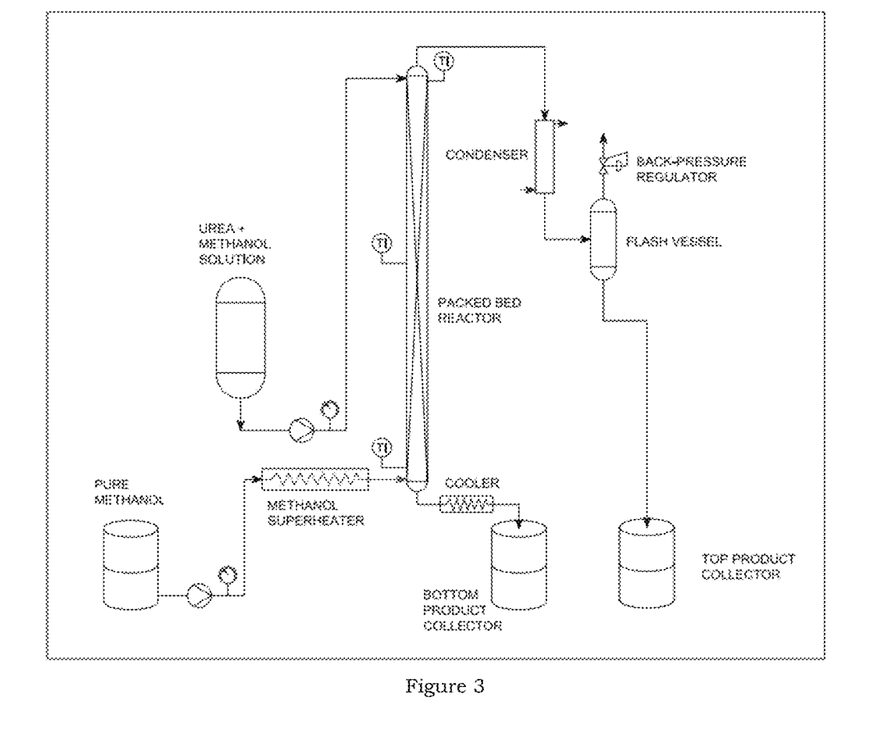
FIG. 3 represents schematic diagram of the bench scale packed bed reactor system. A schematic of the bench scale packed reactor setup is shown in FIG. 3.

In a preferred embodiment of the invention, the process may be realized in a chemical reactor, exemplified herein in a stirred tank reactor of FIG. 3.

Packed Bed Reactor

The facility comprised of a vertical stainless steel tubular reactor of 40 mm I.D and 2 m length. The reaction was carried out at 20 bar pressure in vertical stainless steel tubular reactor of 40 mm I.D and 2 m length (see schematic diagram for details, FIG. 3). The reactor column was packed with high quality randomly-filled metal packings. The tubular reactor was connected to feed vessels. One Vessel contains Urea/MC+MeOH+Catalyst as reaction feed. Another vessel contains only MeOH which is heated in furnace to generate superheated methanol. Superheated methanol is fed to the reactor from the bottom. The difference in weight of feed vessels was measured to know exact amount of material fed to the reactor. During the course of reaction vapors coming out from the top of reactor were condensed (condenser temperature 15° C.) and collected in 10 liter vessel. While the liquid coming from the bottom of the reactor was collected in 2 liter vessel as bottoms. The reactor column was filled with C-shaped SS mesh packing. MC+MeOH+Catalyst solution was fed from top of reactor at room temperature at the rate of 3 ml/min and superheated methanol was fed at 195° C. from the bottom of the reactor. The temperature of the reactor was maintained at 190° C. Product DMC with methanol was collected as an overhead after cooling in a collector and unreacted MC along with catalyst and methanol was collected at the bottom. The fed MC+MeOH+Catalyst solution is in the form of a thin film on SS mesh which interacts with superheated methanol coming from the bottom. The function of superheated methanol is to carry the product DMC and $NH_3$ to the top. For these reactions samples were collected hourly at 1 h interval from the bottom while the overhead sample was collected as a cumulative sample at the end of reaction and analyzed by GC.

At the end of reaction the amount of pure MeOH and MC+MeOH+Catalyst mixture was measured. The amount of reaction mixture collected as overheads and bottoms was measured to account the material balance of the charge fed and collected.

Two experiments each for the step 1 and step 2 i.e. Urea to MC and for MC to DMC were carried out. The results are summarized in Tables 1a and 1b. It can be seen that 100% urea conversion with nearly 94% MC selectivity was achieved (Table 1a, entry 2). The second step was carried out with homogeneous catalyst [$Sm(NO_3)_3$] at 180° C. $Sm(NO_3)_3$ was selected based on the catalyst screening results obtained on 2 liter set up under $N_2$ and methanol feeding conditions at 180° C. (53.6% DMC sel). The process resulted in greater than 57% DMC selectivity with 24.5% MC conversion at 180° C. on packed bed reactor validating stripping and reducing contact of DMC with the catalyst.

TABLE 1a

Urea to MC

| Entry | Temp (° C.) | Time (h) | Charge (g) (Urea + MeOH) | MeOH (g) | Urea Conv (%) | MC Sel(%) | DMC Sel (%) | MMC Sel (%) |
|---|---|---|---|---|---|---|---|---|
| 1 | 190 | 3 | 490 | 884 | 98+ | ~50* (some material was trapped inside the reactor) | 3 | 0.005 |
| 2 | 180 | 5 | 745 | 1578.5 | 100 | 94 | 5 | 1.14 |

Reaction Conditions: MeOH feeding rate 7 ml/min, Urea + MeOH feeding rate 3 ml/min.
Reaction Charge: Urea 264.55 g, MeOH 2367 g, non-catalytic.

TABLE 1b

MC to DMC

| Entry | Temp (° C.) | Time (h) | Charge (g) (MC + MeOH) | MeOH (g) | MCConv (%) | DMC Sel(%) | MMC Sel (%) |
|---|---|---|---|---|---|---|---|
| 1 | 180 | 7 | 1090 | 2605 | 25 | 58 | 2.14 |
| 2 | 180 | 9 | 1415 | 3331 | 32 | 58+ (some material was trapped inside the reactor | 1.44 |

Reaction Conditions: MeOH feeding rate 7 ml/min, MC + MeOH feeding rate 3 ml/min.
Reaction Charge: MC 187.5 g, MeOH 1600 g, $Sm(NO_3)_3$ 8.67 g A shallow bubble column reactor with sparging of superheated methanol from the bottom is disclosed to strip ammonia and DMC from the reaction zone and push the reaction forward and also avoid DME formation.

Bubble Column Reactor

Figure 4:
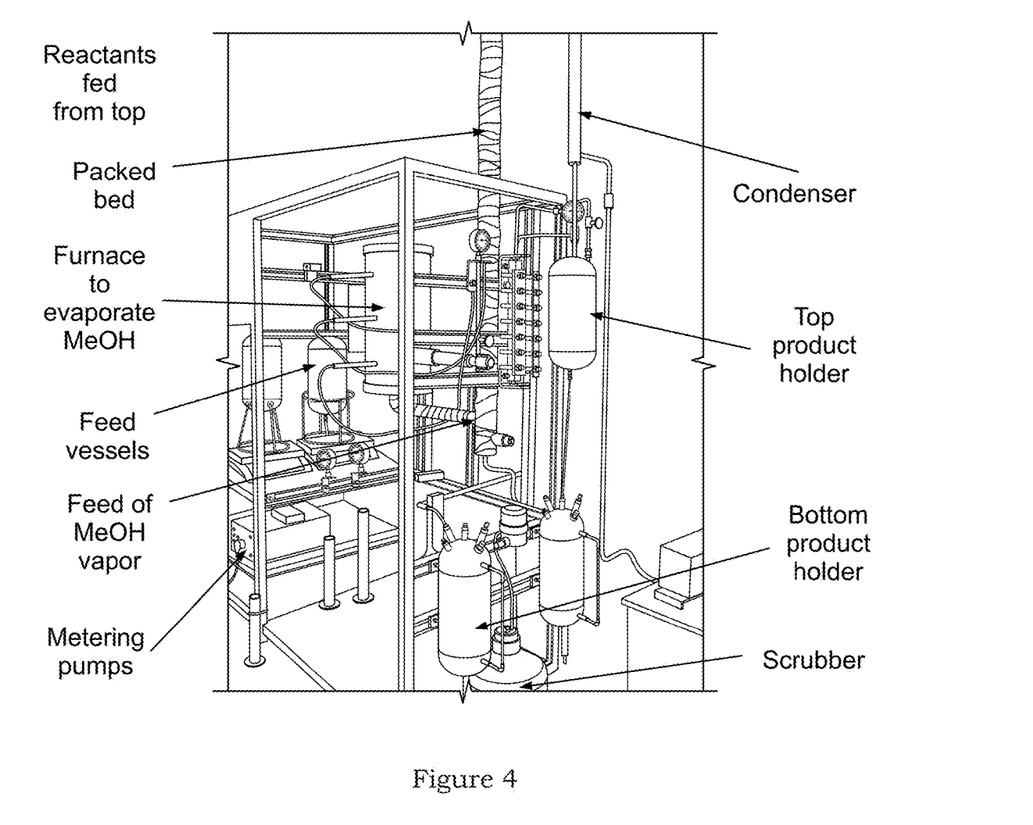
Figure 5:
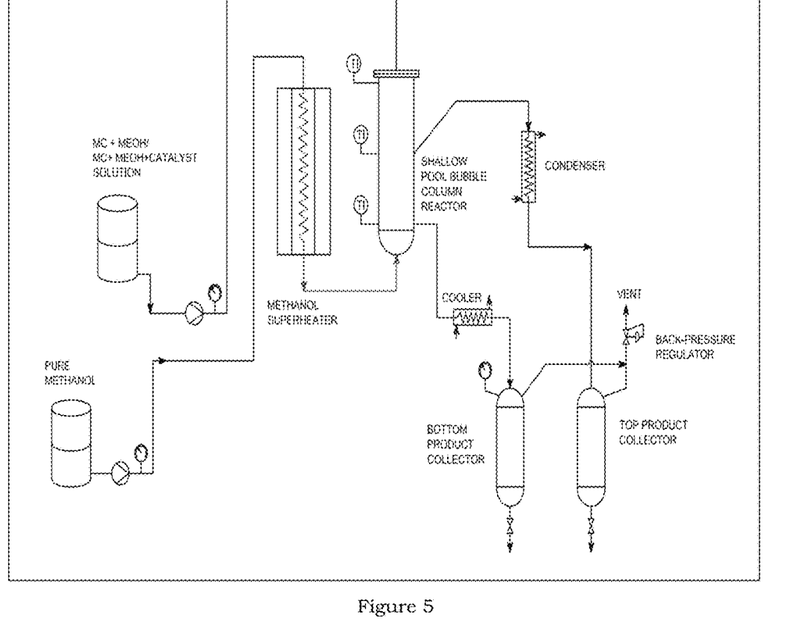
FIG. 5 represents schematic diagram of the bench scale bubble column reactor system is shown in FIG. 5 and FIG.
Figure 6:
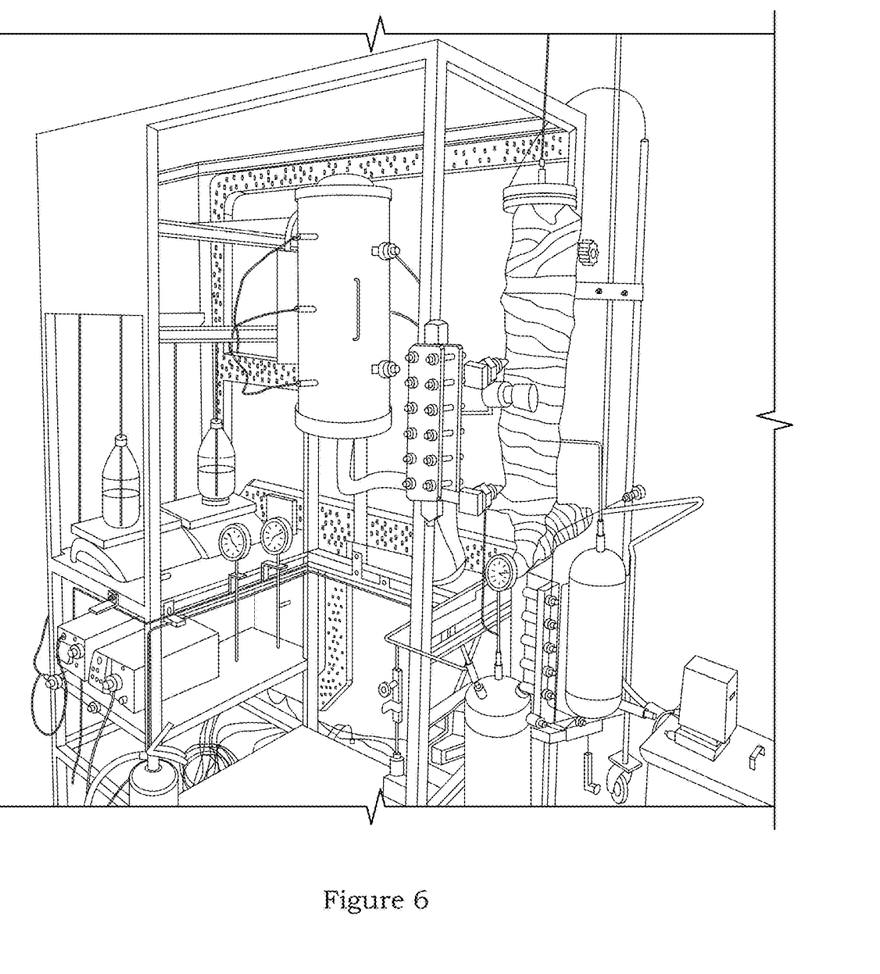

With reference to FIG. 4, the reactions were carried out at 20-24 bar pressure in vertical stainless steel bubble column reactor of 78 mm I.D and 60 cm length (see schematic diagram for details, FIG. 2). The bubble column reactor was connected to feed vessels. One Vessel contains MC+MeOH+Catalyst/MC+MeOH as reaction feed, which is fed to the reactor from top through the dip tube. Another vessel contains pure MeOH, which is fed to the furnace to generate superheated methanol. Superheated methanol is fed to the reactor from the bottom and methanol vapours take ammonia and product DMC quickly out of the reaction mixture and can reduce DME formation. Significant amount of MC also is carried over with methanol vapours and are collected as overhead along with DMC and methanol. The difference in weight of feed vessels was measured to know exact amount of material fed to the reactor. During the course of reaction vapors coming out from the top of reactor were condensed (condenser temperature 15° C.) and collected in overhead vessel. The liquid coming from the bottom of the reactor was collected as bottoms in a separate vessel. MC+MeOH+Catalyst solution was fed from top of reactor at room temperature at the rate of 3-5 ml/min and superheated methanol (195° C.) was fed from the bottom at a flow rate of 7-10 ml/min. The temperature of the reactor was maintained at 185° C. Few experiments were carried out by feeding MC+MeOH+Catalyst solution initially and then it was replaced with MC+MeOH solution. The mixture of MC+MeOH was fed continuously to reactor for a specific reaction time. Product DMC with methanol was collected in overhead collector and unreacted MC along with catalyst and methanol was collected at bottom. For these reactions the samples were collected as cumulative samples from the bottom (MC+methanol) as well as from the top (DMC+Methanol) at the end of reaction and analyzed by GC.

At the end of reaction the amount of pure MeOH and MC+MeOH+Catalyst mixture fed to the reactor was measured. The amount of product mixture collected as overheads and bottoms was measured to estimate the material balance of the charge fed and material collected.

The results on the MC conversion and DMC selectivity using $Sm(NO_3)_3$ as a catalyst are summarized in Table 2 a and b. When the reaction was conducted by continuously feeding MC+MeOH+Catalyst solution to reactor the conversion and DMC selectivity was near about similar compared to the results obtained from packed bed reactor. The results show 32% MC conversion and about 57% DMC selectivity (Table 2a, entry 3). We were able to achieve 67% DMC selectivity and 4% MMC selectivity with 42% MC conversion at 180° C. on bubble column reactor (Table 2a, entry 4). The improvement in selectivity was mainly due to increase in flow rate of superheated methanol from 5 ml/min to 7 ml/min with 3 ml/min flow of reaction feed. This also indicates that efficient removal of DMC is essential to improve selectivity.

One reason for slightly lower selectivity may be high amount of catalyst being fed during the reaction. The liquid level build up is very low and thus catalyst concentration in the reactor increases, which may lead to decomposition of DMC to DME. To avoid this, few experiments were carried out with the addition of catalyst at the start of the reaction. For this purpose MC/Methanol/catalyst solution (Methanol: MC ratio: 5:1) was first fed to the reactor till 3.5 g catalyst was charged and desired liquid level in the reactor was attained. Afterwards the feed was changed to Methanol/MC (flow rate 3 ml/min) and reaction was continued. In these experiments superheated methanol flow was kept at 7 ml/min. From the results it can be seen that 66% DMC selectivity and 4% MMC selectivity with 43% MC conversion was achieved (Table 2b, entry 1). A slight decrease in DMC selectivity (62.5) and MC conversion (40.5) could be seen (Table 2b, entry 2) when the reaction was carried out by reducing the MC to methanol ratio (MC:MeOH=1:5). Another reaction was carried out by increasing the flow rate of superheated methanol to improve efficiency of stripping of ammonia and DMC formed in the. It can be seen that 75% DMC selectivity and 4.4% MMC selectivity with 34% MC conversion was achieved (Table 2b, entry 3). This clearly indicates that efficient removal of ammonia and DMC is essential to improve selectivity to DMC and avoid DME formation. This is the best DMC selectivity achieved so far for our reaction and the selectivity is comparable with the results reported in the literature.

One experiment for urea to MC was carried out on bubble column reactor at low urea: methanol ratio (1:7.5). It can be seen that about 83% urea conversion and 93% MC selectivity was obtained (Table 2c, entry 1).

TABLE 2a

MC to DMC (MC + MeOH + $Sm(NO_3)_3$ was fed continuously to reactor)

| Entry | MC:MeOH ratio | Catalyst (g) | Time (h) | Charge (g) | | Feeding rate (ml/min) | | MC Conv (%) | DMC Sel(%) | MMC Sel (%) |
|---|---|---|---|---|---|---|---|---|---|---|
| | | | | (MC + MeOH) | MeOH (g) | MC + MeOH | MeOH | | | |
| 1[a] | 1:20 | 8.45 | 4 | 1728 | 2357 | 5 | 7 | 50.0 | 40.0 | 2.0 |
| 2[b] | 1:10 | 6.95 | 6 | 1570 | 2452 | 5 | 7 | 15.9 | 35.3 | 0.8 |
| 3[b] | 1:10 | 6.89 | 7 | 1556 | 2378 | 5 | 5 | 32.0 | 56.9 | 4.5 |
| 4[b] | 1:10 | 5.93 | 6 | 1339 | 2857 | 3 | 7 | 42.1 | 67.2 | 4.1 |

Reaction Conditions: Temp., 185° C.
Reaction Charge:
[a]MC 187.5 g, MeOH 1600 g and $Sm(NO_3)_3$ 8.75 g;
[b]MC 375 g, MeOH 1600 g and $Sm(NO_3)_3$ 8.75 g TABLE 2b MC to DMC (MC + MeOH + Sm(NO$_3$)$_3$ was fed initially to reactor)

| Entry | MC:MeOH ratio | Catalyst (g) | Time (h) | Charge (g) (MC + MeOH) | MeOH (g) | Feeding rate (ml/min) MC + MeOH | MeOH | MC Conv (%) | DMC Sel(%) | MMC Sel (%) |
|---|---|---|---|---|---|---|---|---|---|---|
| 1[a] | 1:10 | 3.5 | 6 | 1499 | 2611 | 3 | 7 | 43.1 | 65.8 | 4.0 |
| 2[b] | 1:5 | 3.5 | 6 | 1493 | 2747 | 3 | 7 | 40.5 | 62.5 | 5.3 |
| 3[b] | 1:5 | 3.5 | 6 | 1530 | 4030 | 3 | 10 | 34.0 | 75.0 | 4.4 |

Reaction Conditions: Temp., 185° C.
Reaction Charge:
[a]MC 375 g, MeOH 1600 g and Sm(NO$_3$)$_3$ 3.5 g,
[b]MC 750 g, MeOH 1600 g and Sm(NO$_3$)$_3$ 3.5 g TABLE 2c Urea to MC

| Entry | Temp (° C.) | Time (h) | Charge (g) (Urea + MeOH) | MeOH (g) | Urea Conv (%) | MC Sel(%) | DMC Sel (%) | MMC Sel (%) |
|---|---|---|---|---|---|---|---|---|
| 1 | 170 | 6.45 | 1820 | 2504 | 92.7 | 83.1 | 1.3 | 0.17 |

Reaction Conditions: MeOH feeding rate 7 ml/min, Urea + MeOH feeding rate 5 ml/min.
Reaction Charge; Urea g, MeOH g Urea:MeOH, 1:7.5, non-catalytic.

EXAMPLES

Following examples are given by way of illustration and therefore should not be construed to limit the scope of the invention.

Example 1

Urea 7.5 g (120 mmol) and methanol 64 g (2000 mmol) was charged to a 300 ml reactor connected to a 2 liter nitrogen reservoir from gas inlet valve. The reservoir is fitted to reactor through constant pressure regulator which is set at 400 psi. A back pressure regulator was fitted to reactor at gas outlet valve. Back pressure regulator is set at 390 psi. The pressure difference of 10 psi was maintained between constant pressure regulator and back pressure regulator to ensure positive flow of nitrogen. This allows stripping of CH$_3$OH along with NH$_3$ that is formed during reaction. The reactor was then pressurized with nitrogen atmosphere at 400 psi. The inlet valve was closed at this point keeping outlet valve open. The contents were heated to 180° C. under very slow stirring condition. After attaining the temperature the inlet valve was opened. The reaction was continued 2 h. During this period methanol along with NH$_3$ was expelled due to the set positive pressure of nitrogen. This methanol along with dissolved NH$_3$ was collected in a collection vessel (cooled with ice and salt mixture) connected to BPR outlet. After completion of reaction the reactor was cooled to room temperature. Reaction mixture from bomb (autoclave) as well as from collection vessel (trap) was analyzed separately by HPLC and Gas Chromatography for urea and MC analysis respectively. From HPLC and GC analysis 97.8% conversion of urea and 89.4% selectivity to MC and 1.9% selectivity to DMC was observed in the reaction. Under above mentioned identical conditions when reaction was carried out without nitrogen sparging the selectivity to MC was found to be 68% (with somewhat lower conversion of urea).

Example 2

The procedure same as mentioned in EXAMPLE 1 was followed. Except that this reaction was carried out for 1 h. After completion of reaction mixtures from bomb as well as trap were analyzed by HPLC and GC which showed 95.82% conversion of urea and 80.81% selectivity to MC and 2.4% selectivity to DMC.

Example 3

Similar to EXAMPLE 1 except the reaction was carried out for 30 min. The HPLC and GC analysis showed 95.6% conversion of urea and 83.9% selectivity to MC and 1.2% selectivity to DMC.

Example 4

Similar to EXAMPLE 1 except this reaction was carried out using higher nitrogen flow for and reaction time was reduced to 10 min. This reaction was carried out to substantiate the effect of high N$_2$ flow. The HPLC and GC analysis of both reaction mixtures showed 82.1% conversion of urea and 91.5% selectivity to MC and 0.4% selectivity to DMC.

Based on examples 2 to 4, it can be seen that with nitrogen sparging, substantial enhancement in the overall rate of reaction could be realized.

Example 5

Similar to EXAMPLE 1 except this reaction was carried out at 160° C. with higher nitrogen flow. The HPLC and GC analysis of both reaction mixtures showed 97.4% conversion of urea and 98.8% selectivity to MC. Under above mentioned identical conditions when reaction was carried out without nitrogen sparging 88.7% conversion of urea and 91.1% selectivity to MC was observed.

Example 6

Methyl carbamate (MC) 7.5 g (100 mmol), methanol 64 g (2000 mmol) and 1 g of $ZnCl_2$ as catalyst was charged to a 300 ml reactor connected to a 2 liter nitrogen reservoir from gas inlet valve. The reaction was carried out for 2 h with methanol dosing. For this purpose a syringe pump was attached to the reactor through sampling valve. The reservoir is fitted to reactor through constant pressure regulator which is set at 400 psi. A back pressure regulator was fitted to reactor at gas outlet valve. Back pressure regulator is set at 390 psi. The pressure difference of 10 psi was maintained between constant pressure regulator and back pressure regulator to ensure positive flow of nitrogen. This will help in stripping of $CH_3OH$ along with $NH_3$ that is formed during reaction. The reactor was then pressurized with nitrogen atmosphere at 400 psi. The inlet valve was closed at this point keeping outlet valve open. The contents were heated to 180° C. under very slow stirring condition. After attaining the temperature the inlet valve was opened and methanol dosing was started at the rate of 1 ml/min. The GC analysis of reaction mixture showed 64.6% conversion of MC and 24.7% selectivity to DMC. Under above mentioned identical conditions when reaction was carried out without nitrogen sparging 37% conversion of MC was observed in the reaction.

ADVANTAGES OF INVENTION

By selecting appropriate composition and flow rate of inert gas, overall performance of synthesis of MC or DMC process can be tailored and improved.

The rate as well as selectivity towards MC or DMC can be tailored and improved. Applicable to MC synthesis with or without any catalyst and DMC synthesis with any catalyst (homogeneous or heterogeneous).

The use of bubble column allows cross-flow stripping. The disclosed way of stripping DMC and ammonia is significantly better than counter-flow stripping in packed column or mixed stripping in stirred reactor.

Sectionalized horizontal bubble column reactor configuration further improves the efficacy of the cross-flow stripping and therefore improves performance.

Sectionalized horizontal bubble column reactor also offers unprecedented flexibility and versatility to carry out DMC reactions.

The bubble column reactor of the instant invention outperforms other forms of stripping. The performance of stripping can be checked by the conversion achieved. Higher the conversion obtained higher is the performance of stripping.

Thus the invention discloses a process of synthesis of MC and DMC using counter current or cross-flow stripping (using packed column reactor, bubble column reactor or horizontal sectionalized bubble column reactor for this purpose). The key features of the disclosed invention are:

Though stripping of ammonia is known to enhance DMC selectivity, the disclosed configuration offers significantly better stripping (performance of bubble column reactor [cross flow stripping] is much better than that of packed column [counter-current stripping] or that of stirred reactor Not only stripping of ammonia is carried out, but also stripping of DMC. The stripping of DMC further enhances reaction rates and selectivity. In one of the embodiments, there is no liquid outlet (reactants enter in liquid phase and products leave the reactor in vapor form).

The disclosed invention also highlights use of (super-heated or otherwise) methanol vapors for stripping. This eliminates use of extraneous (to the reaction system) gas for stripping and therefore offers several economic advantages by eliminating costly separation steps.

Stripping of ammonia does not prevent decomposition of DMC to other side products such as dimethyl ether or MMC. Therefore, though stripping of ammonia pushes reaction in forward direction, it will not improve the selectivity of DMC. The striping of DMC as disclosed in this invention will significantly reduce decomposition of DMC to DME or formation of MMC and will enhance selectivity towards DMC.

Concept of sectionalized horizontal bubble column allows cross-flow stripping. This disclosed way of stripping DMC and ammonia is significantly better than counter-flow stripping in packed column or mixed stripping in stirred or reactor.

Sectionalized horizontal bubble column reactor also offers unprecedented flexibility and versatility to carry out DMC reactions. Urea to MC and MC to DMC steps can be combined in a single vessel comprising different sections. This also allows manipulation of pressure and temperature of different sections to minimize utility consumption while improving the selectivity.

The invention claimed is:

1. A process for synthesis of methyl carbamate and dimethyl carbonate (DMC) in a reactor, the process comprising:
   a. feeding a liquid reactant feed comprising urea and methanol or methyl carbamate and methanol into a reactor vessel containing a catalyst, wherein the catalyst is either a heterogeneous catalyst in a form of an expanded slurry bed of solid catalyst particles suspended in a suspension liquid or in a packed bed of solid catalyst, or a homogenous catalyst, wherein the homogenous catalyst is a samarium nitrate catalyst dissolved in the liquid reactant feed present in the reactor, and allowing the liquid reactant feed and the catalyst to react in the reactor vessel;
   b. passing inert gas or superheated methanol vapours into the reactor vessel through an inlet valve by regulating a pressure to ensure positive flow of the inert gas or superheated methanol vapours, and stripping ammonia and DMC formed during a reaction in the reactor vessel through an outlet port;
   c. passing the ammonia and DMC collected from the outlet port through a condenser and a gas-liquid separator;
   d. removing liquid phase products from the reactor vessel through a liquid outlet post; and
   e. recycling a stream of methanol or gaseous product leaving the gas-liquid separator into the reactor vessel for further reaction, through an inlet port.

2. The process according to claim 1, wherein the reactor used is selected from packed bed reactors and bubble column reactors having counter-current and cross-current stripping.

3. The process according to claim 1, wherein the catalyst is a heterogeneous catalyst selected from the group consisting of hydrotalcite, double metal cyanides, and cenospheres.

4. The process according to claim 1, wherein a concentration of the catalyst particles present in the slurry bed is in a range of 0.01 to 10 weight percentage.

5. The process according to claim 1, wherein the inert gas is selected from air, $CO_2$, He, Ar, and $N_2$.

6. The process according to claim 1, wherein a velocity of the inert gas or superheated methanol vapors used for stripping the ammonia and DMC is in a range of $1\times10^{-4}$ to 0.1 m/s.

7. The process according to claim 1, wherein the pressure in step (b) is regulated by maintaining a constant pressure difference between a constant pressure regulator fitted to the inlet valve and a back pressure regulator fitted to the outlet port to ensure positive flow of the inert gas.

8. The process according to claim 1, wherein the reactor is maintained at a temperature in a range of 130-210° C.

9. The process according to claim 1, wherein the process is batch or continuous.

10. The process according to claim 1, wherein a ratio by weight of the stream of the methanol or gaseous product leaving the gas-liquid separator and recycled into the reactor vessel to the liquid reactant feed is in a range of 0.5 to 15.

11. The process according to claim 1, wherein the reactor is a bubble column reactor selected from horizontal bubble column and horizontal sectionalized bubble column reactors.

* * * * *